(12) United States Patent
Murphy et al.

(10) Patent No.: US 9,000,251 B2
(45) Date of Patent: Apr. 7, 2015

(54) DRAINING WOUND DRESSING

(75) Inventors: Christopher Murphy, Vass, NC (US); Corey Russ, Fayetteville, NC (US); Jim McGuire, Westerville, OH (US)

(73) Assignee: Combat Medical Systems, LLC, Fayetteville, NC (US)

( * ) Notice: Subject to any disclaimer, the term of this patent is extended or adjusted under 35 U.S.C. 154(b) by 291 days.

(21) Appl. No.: 13/210,193

(22) Filed: Aug. 15, 2011

(65) Prior Publication Data

US 2012/0165715 A1    Jun. 28, 2012

Related U.S. Application Data

(60) Provisional application No. 61/377,379, filed on Aug. 26, 2010.

(51) Int. Cl.
*A61F 13/00* (2006.01)
*A61F 13/02* (2006.01)

(52) U.S. Cl.
CPC .................................... *A61F 13/023* (2013.01)

(58) Field of Classification Search
USPC .................................... 602/41–43, 52, 54, 57
See application file for complete search history.

(56) References Cited

U.S. PATENT DOCUMENTS

| | | | |
|---|---|---|---|
| 4,334,530 A * | 6/1982 | Hassell | 602/42 |
| 4,465,062 A | 8/1984 | Versaggi et al. | |
| 4,717,382 A | 1/1988 | Clemens et al. | |
| RE33,353 E * | 9/1990 | Heinecke | 428/41.5 |
| 5,106,362 A | 4/1992 | Gilman | |
| 5,160,322 A | 11/1992 | Scheremet et al. | |
| 5,263,922 A | 11/1993 | Sova et al. | |
| 5,358,494 A | 10/1994 | Svedman | |
| 5,431,633 A | 7/1995 | Fury | |
| 5,478,333 A | 12/1995 | Asherman, Jr. | |
| 5,662,598 A | 9/1997 | Tobin | |
| 7,504,549 B2 | 3/2009 | Castellani et al. | |
| 7,615,674 B2 | 11/2009 | Asherman | |
| 2007/0232978 A1 | 10/2007 | Castellani et al. | |
| 2008/0033377 A1 | 2/2008 | Kauth et al. | |

OTHER PUBLICATIONS

European Search Report dated Nov. 15, 2011, EP Application No. 11006897.0.

\* cited by examiner

*Primary Examiner* — Victoria J Hicks
*Assistant Examiner* — Caitlin Carreiro
(74) *Attorney, Agent, or Firm* — Knobbe Martens Olson & Bear LLP (57) ABSTRACT

A wound dressing is made of multiple layers and includes a collection chamber that is in fluid communication with a drainage channel. When applied over a wound, the wound dressing provides protection for the wound while allowing air and fluids to evacuate from the wound through the collection chamber and out through the drainage channel. The wound dressing can include a valve that restricts air and fluids from entering the wound, which is beneficial for treating pneumothorax.

18 Claims, 7 Drawing Sheets

DRAINING WOUND DRESSING

RELATED APPLICATIONS

The present application claims priority under 35 U.S.C. §119(e) to U.S. Provisional Application No. 61/377,379 filed on Aug. 26, 2010, the disclosure of which is incorporated by reference herein in its entirety.

TECHNICAL FIELD

The present invention relates generally to medical wound dressings, and more specifically to wound dressings that allow fluids and exudates from the wound to drain away from the wound.

BACKGROUND

Wound dressings have significantly contributed to increased survivability from physical trauma by helping to control bleeding and protect the wound from entry of bacteria or other infective agents. Typically, wound dressing are generally flexible materials, such as gauzes, bandages, fabrics, etc., that can be used to treat wounds. In combat situations, wounds are often life-threatening and the time pressures associated with treating wounds may be amplified by ongoing hostilities. Especially prevalent on the combat battlefield are penetrating wounds that can be caused by gunshots or shrapnel.

Previous attempts to provide a quick and easily deployable device to treat wounds have included gauzes with an adhesive side that can be applied directly over wounds. Unfortunately, the pressure of the blood and fluids exuding from the wounds has allowed the fluids to seep in-between the skin and adhesive, thereby eventually separating the adhesive from the skin.

Also, in some situations, a condition known as a pneumothorax, also known colloquially as a "collapsed lung," can occur with a penetrating wound. The outer portion of the lung is composed of two tissue layers: the internal visceral pleura that cover the lungs, and the external parietal pleura that is attached to the chest wall. The space between the visceral and parietal pleura is known as the pleural space. Under normal conditions, the visceral and parietal pleura are nearly flush against one another with the pleural space usually containing only a thin layer of pleural fluid. However, when an aperture to the pleural space is created by a penetrating chest wound, air or fluids can enter the pleural space and the resulting air or fluid pocket can compress the inner portion of the lung, making breathing extremely difficult.

Pneumothoracies are generally classified into two types: tension and non-tension. The latter can occur with trauma, various illnesses, or even spontaneously. While non-tension pneumothorax can lead to chest pain and difficulty breathing because the lung is incapable of expanding fully, it is generally of lesser concern than tension pneumothorax, which is a medical emergency. A tension pneumothorax occurs when a penetrating chest wound effectively forms a one-way valve into the chest cavity that allows airflow into the pleural space while preventing airflow out. In a tension pneumothorax, each inhalation traps air in the chest, increasing pressure on the lungs and ultimately causing them to collapse. In some cases, one lung can be pushed into the heart and the other lung, interfering with the functions of these organs. As the blood vessels of the lung are compressed, the vascular pressure increases and puts pressure on the right ventricle of the heart, possibly leading to cardiac failure.

Some wound dressings were designed to prevent the intake of air and/or fluid into the chest cavity for penetrating chest wounds. However, these dressings are inadequate for battlefield environments, where extreme rigors and demands are placed on medical equipment and personnel. Common failures of these devices during combat conditions can range from inadequate adhesive for attaching to the skin, insufficient size for covering large wounds, complexity of use, and length of time needed to deploy the bandage.

SUMMARY OF THE DISCLOSURE

In some embodiments, wound dressings for a penetrating wound are capable of maintaining an effective shield over the wound which blocks fluid and dirt from entering the wound while allowing fluid outflow. The dressings are able to remain attached to the patient and withstand the jostling of the patient under the extreme rigors of combat conditions. In some embodiments, dressings for penetrating chest wounds are provided that are quick and easy to apply over the wound.

Thus, in accordance with some embodiments of the present application, the draining wound dressing can comprise a base layer comprising a first aperture extending through the base layer. A first adhesive layer can be coupled to a first side of the base layer and comprise a second aperture extending through the first adhesive layer. A second adhesive layer can be coupled to a second side of the base layer and comprise a third aperture extending through the second adhesive layer. A channel layer can comprise at least one member coupled to portions of the second adhesive layer. A top layer can be coupled to at least portions of the second adhesive layer and apposed to or brought into contact with the channel layer, wherein a channel is formed between the channel layer and the top layer, the channel extending from the third aperture to an edge of the second adhesive layer. The first aperture, second aperture, and third aperture are generally aligned to form a collection chamber that is in fluid communication with the channel.

In some embodiments, the wound dressing can comprise a liner layer coupled to the first adhesive layer. In some embodiments, the wound dressing can further comprise a print layer coupled to or positioned above the top layer. The print layer can be applied to lower layers when at least a portion of one or more higher layers is transparent.

In some embodiments, the wound dressing can comprise at least one valve that restricts air and fluids from entering the wound. In some embodiments, the wound dressing can further comprise a drainage channel member and a vent channel member.

In accordance with some embodiments of the present application, the draining wound dressing can comprise a first layer, a second layer over the first layer, a third layer over the second layer, a fourth layer over the third layer, and a collection chamber formed by an aperture extending through the first layer, second layer and third layer. In some embodiments, the draining wound dressing can further comprise a fifth layer disposed in at least portions between the third layer and fourth layer, wherein a channel is formed between the fourth layer and fifth layer that extends from the collection chamber to an edge of the wound dressing and wherein the channel is in fluid communication with the collection chamber.

In accordance with some embodiments of the present application, a method of treating a wound can comprise the step of opening a package containing a wound dressing, the wound dressing comprising at least four layers and having a collection chamber and a drainage channel. The wound dressing can be prepared by exposing a first adhesive layer that is configured to attach to skin. The wound dressing can be oriented using an indicator visible on the wound dressing so that the drainage channel is directed generally downward in the direction of gravity. The dressing can be placed on a patient so that the collection chamber is generally centered over the wound.

DETAILED DESCRIPTION OF SPECIFIC EMBODIMENTS

Figure 1:
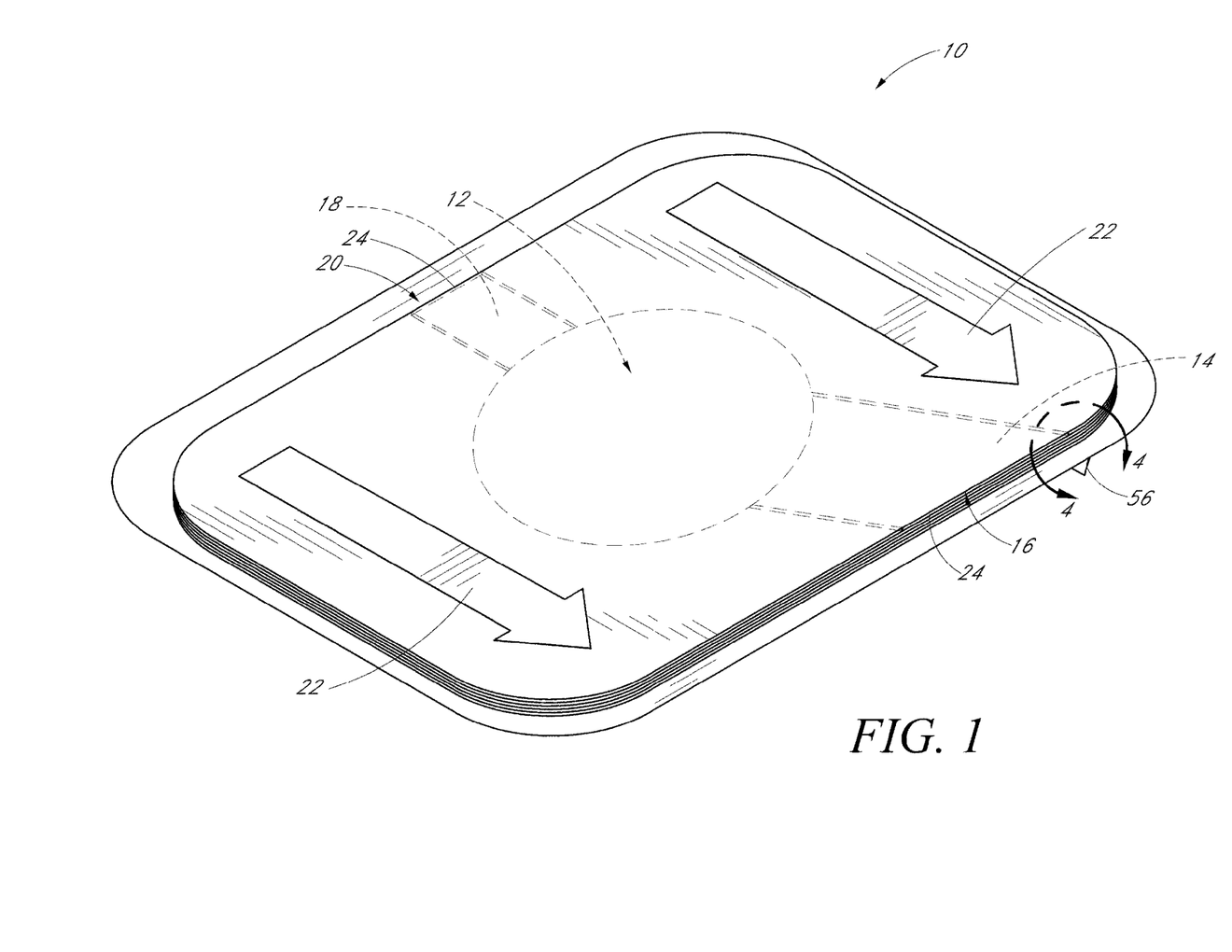
FIG. 1 is a schematic top perspective view of a wound dressing according to an embodiment of the present application.
Figure 2:
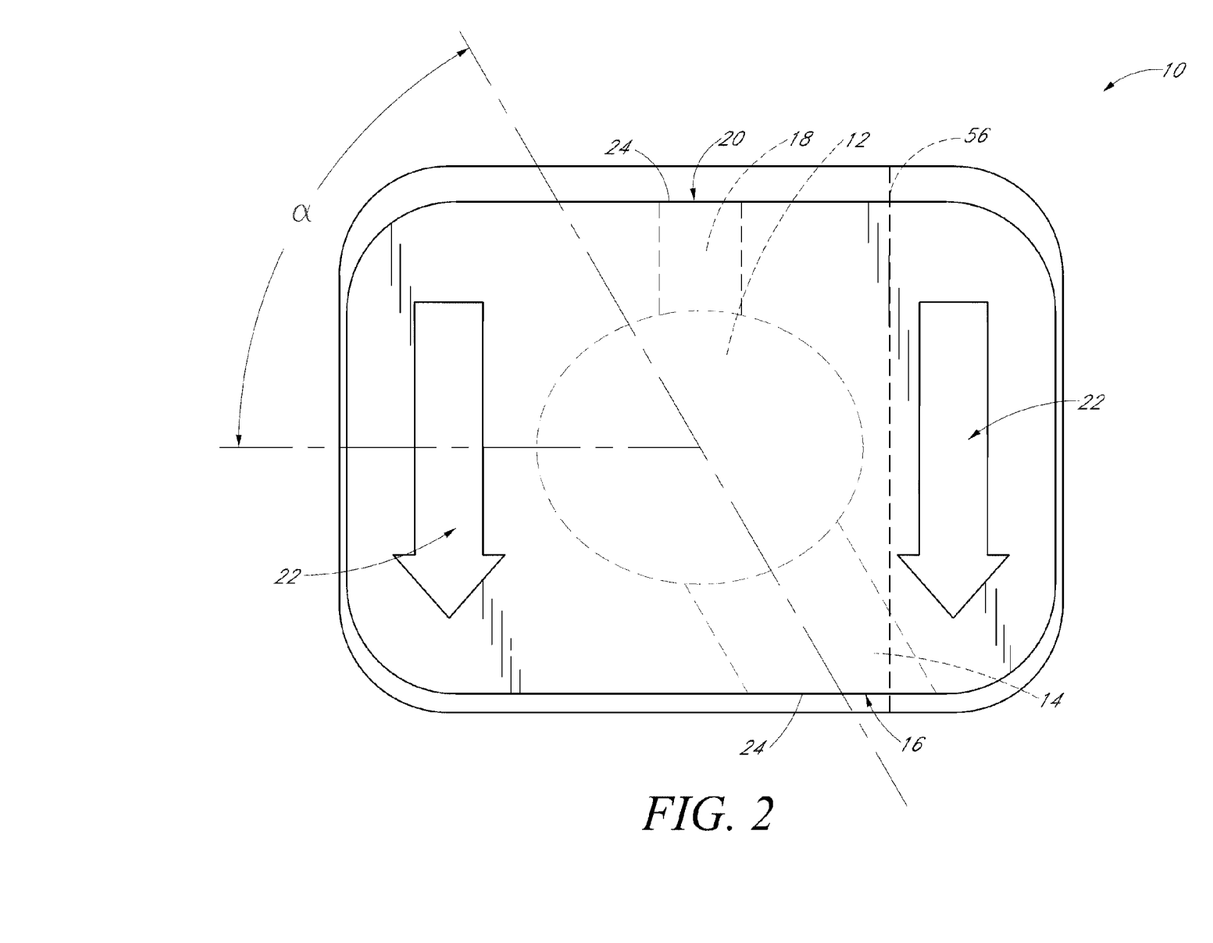
FIG. 2 is a schematic top plan view of the wound dressing of FIG. 1.

With reference to the drawings, several examples of devices will now be described in more detail. FIGS. 1 and 2 illustrate an embodiment of a wound dressing 10 that allows fluids and exudates from the wound to drain away from a wound site. In the illustrated embodiment, the wound dressing 10 has several layers on top of one another and has a generally rectangular shape with rounded corners when viewed from the top. The overall thickness of the device can advantageously be thin enough to provide the wound dressing sufficient flexibility to comfortably bend and stretch to conform to the patient's skin surface. In some embodiments, the overall thickness of the wound dressing can be less than approximately 0.15 mm and in some embodiments can be approximately 0.1 mm. In one example, the overall length can be approximately 168 mm and the overall width can be approximately 127 mm. However, many sizes and shapes can be used to suit particular applications and methods of manufacturing and the wound dressing 10 is not limited to a particular shape or size.

The wound dressing 10 can have a collection chamber 12 that is open at the bottom side of the wound dressing 10 and extends through multiple layers, but is enclosed on top by one of the layers. In use, the collection chamber 12 can be configured to be positioned over the wound to receive or collect the exudates from the wound. Although illustrated in the figures as positioned toward the middle of the wound dressing, in some embodiments the collection chamber 12 can be positioned off-center on the wound dressing 10. In the illustrated embodiment, the collection chamber 12 has a generally ovular shape. In some embodiments, the length of the major axis of the ovular chamber can be approximately 76 mm and the length of the minor axis of the ovular chamber can be approximately 64 mm. In some embodiments, the cross-sectional width of the chamber in one or more dimensions is at least about 40 mm and/or less than or equal to about 100 mm. In some embodiments, the collection chamber 12 is generally or entirely round or circular. In some embodiments, the collection chamber 12 can be of any size and have any shape, such as circular, square, rectangular, polygonal, or other shape. The size of the collection chamber is intended to generally correspond to the size of the chest wound most commonly treated with the chest dressing.

A drainage channel 14 can be in fluid communication with the collection chamber 12 and extend to a drainage channel outlet 16 at or near the periphery of the wound dressing 10. In some embodiments, the would dressing 10 can have a vent channel 18 that is in fluid communication with the collection chamber 12 and extends to a vent channel outlet 20 at or near the periphery of the wound dressing 10. In the illustrated embodiment, the drainage channel 14 extends from the collection chamber 12 toward one side of the wound dressing 10 and the vent channel 18 extends from the collection chamber 12 toward an opposite side of the wound dressing 10. In some embodiments, the vent channel 18 can extend to a side of the wound dressing 10 that is perpendicular to the side towards which the drainage channel 14 extends.

The wound dressing 10 can have an indicator 22 that informs medical personnel of the orientation in which the wound dressing 10 is to be applied on the patient. In some embodiments, the indicator 22 can illustrate the intended general direction of flow of fluids through the wound dressing 10. In the illustrated embodiment, the wound dressing 10 can be applied on the patient such that the indicator arrows 22 generally point down in the direction of gravity, allowing fluids from the wound to flow out the drainage channel 14. In some embodiments, the indicator 22 can be other marks, symbols, labels, etc., that indicate to the user the desired orientation for affixing the wound dressing 10 on the patient. The packaging, directions for use, or other instructions can instruct the user to orient the wound dressing generally downwardly to permit more effective drainage and to diminish the risk of accumulating too much exudates in the collection chamber 12.

Figure 3:
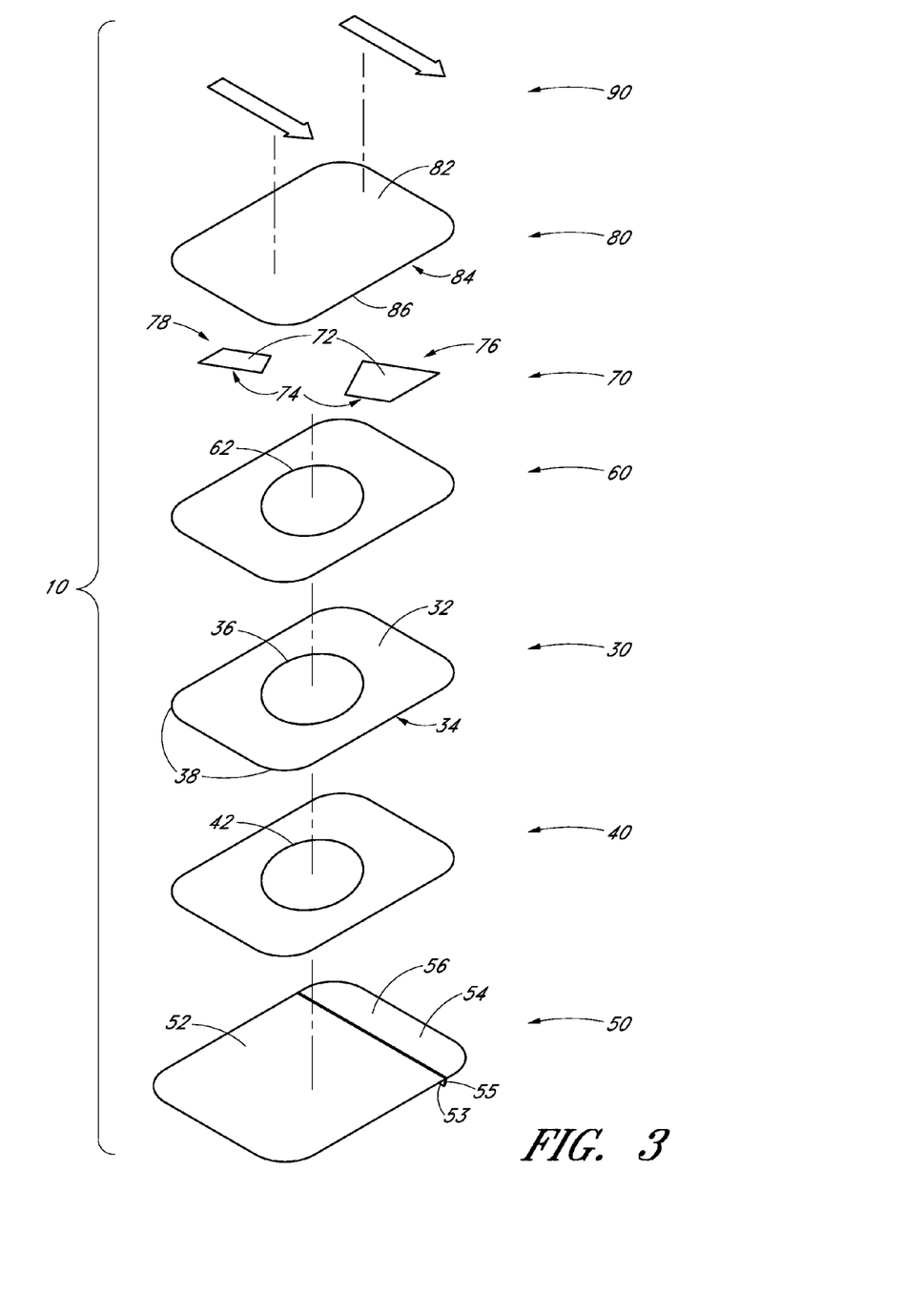
FIG. 3 is a schematic exploded top perspective view of the wound dressing of FIG. 1.

With reference to FIG. 3, the wound dressing 10 can be constructed of several layers of thin materials that are coupled together through any suitable methods, such as for example using adhesives, staples, sonic welding, rivets, clamps, etc. The wound dressing 10 can be made of flexible materials that can conform to the contours of the patient's body and promote the sealing of the wound dressing 10 around the wound. In some embodiments, some or all of the layers can be at least partially or entirely transparent so that medical personnel can inspect the wound site and determine the effectiveness of the wound dressing 10. Although the illustrated embodiment has seven layers, other embodiments can have more or fewer layers to suit particular applications. Some layers can be omitted while other additional layers can be included. In some embodiments, a single layer can serve the function of two or more separate layers, as described below.

In the illustrated embodiment, the wound dressing 10 has a base layer 30 in the middle of the stack of layers. Attached to a bottom surface 34 of the base layer 30 can be a skin adhesive layer 40 that is configured to adhere to a patient's skin. A protective liner layer 50 can be coupled to the bottom surface of the skin adhesive layer 40 to protect the adhesive material from dirt and contamination, and to avoid unintended sticking before use. On the top surface 32 of the base layer 30 can be a top adhesive layer 60. Above at least a portion of the top adhesive layer 60 can be a channel layer 70 that is in the location and shape of the drainage channel 14 and vent channel 18. A top layer 80 can be disposed above the channel layer 70 that attaches to portions of the top adhesive layer 60 and is adjacent the channel layer 70. Over the top layer 80 can be a print layer 90 which includes the figures, marks, symbols, labels, etc.

Although described with a particular combination of layers, some embodiments can have other combinations and/or arrangement of layers to produce similar functions as those described herein, as would be understood by one of skill in the art.

With reference to FIG. 3, in some embodiments, base layer 30 can be a generally rectangular sheet formed from a generally fluid impermeable plastic and having a top surface 32 and bottom surface 34. In the illustrated embodiment, the length of the base layer 30 is approximately 165 mm and the width is approximately 114 mm. In some embodiments, either or both of the length or width of the device, or any layers therein, can be at least about 75 mm and/or less than or equal to about 200 mm. However, many sizes and shapes can be used to suit particular applications and methods of manufacturing, and neither the device 10 nor any layers therein are limited to a particular shape or size.

In some embodiments, the base layer 30 can be made of a flexible plastic, such as polyurethane film. In some embodiments, the base layer 30 and/or any other layer of the device 10, can be made of other plastics, metals (e.g., foils), textiles (e.g., gauze, cloth, etc.), composites, or other suitable materials. In some embodiments, the base layer 30 can be at least partially transparent to allow visual inspection of the wound site through the wound dressing 10. Any layer, or other portion, of the device 10 can include one or more therapeutic agents, such as hemostatic, anti-microbial, anti-biotic, anti-fungal, anti-septic, or anesthetic agents.

In some embodiments, the base layer 30 has sufficient thickness to provide structural strength to resist tears, while being compliant to conform to the contours of the patient's body. For example, the flexible nature of the base layer 30 can help the wound dressing 10 to stretch and bend as the patient's skin moves. In some embodiments, the thickness of the base layer 30 can be approximately 6 mil. In some embodiments, the thickness can range from approximately 1 mil to approximately 10 mil.

In the middle portion of the base layer 30 can be an opening or a cutout 36 that forms a portion of the collection chamber 12. Although the opening or cutout 36 is shaped as an oval in the illustrated embodiment, in some embodiments the opening or cutout 36 can have any size or shape, such as circular, square, rectangular, polygonal, or other shape.

As illustrated in the figures, the corners 38 of the rectangular sheet can be generally rounded or chamfered, which can help prevent the corners from becoming snagged on other objects. The rounded corners 38 can also help prevent the corners from pulling away from the patient's skin. For example, a sharp corner generally has a point where adjacent sides of the dressing converge. The point does not provide much surface area to apply the skin adhesive, resulting in a spot of the wound dressing that is not well adhered to the patient's skin. This spot may tend to detach and peel up from the patient in the presence of blood, sweat, or other liquids, producing a weak region of adhesion that can grow until the device produces a leak or falls entirely off the patient. A rounded corner, on the other hand, does not have a sharp point where the adhesive can easily separate from the skin. The adhesive is thus better able to hold the rounded corners of the wound dressing 10 to the patient's skin. In some embodiments, the radius of the rounded corners 38 can be approximately 25 mm. In some embodiments, the radius of the rounded corners can range from approximately 10 mm to approximately 40 mm.

Below the base layer 30 can be a skin adhesive layer 40 which is attached to the bottom surface 34 of the base layer 30. The skin adhesive layer 40 can have generally the same size and shape as the base layer 30 so that it covers generally the entire bottom surface 34 of the base layer 30. An opening or a cutout on the skin adhesive layer 42, similar in shape and size to the opening or cutout 36 on the base layer 30, can be disposed on the skin adhesive layer 40.

Sufficient adhesive material can be provided in the skin adhesive layer 40 to provide firm adhesion to the skin of a patient. In some embodiments, the thickness of the skin adhesive layer 40 can fill in or otherwise accommodate imperfections on the patient's skin, such as wrinkles, bumps and folds. In some embodiments, the thickness of the skin adhesive layer 40 can be approximately 6 mil. In some embodiments, the thickness can range from approximately 1 mil. to approximately 10 mil. In some embodiments, the skin adhesive layer 40 may not cover the entire bottom surface 34. For example, the skin adhesive layer can be a bead of adhesive that extends along the outer perimeter of the bottom surface 34 and the perimeter of the cutout 36. In many embodiments, at least the skin adhesive layer 40 and/or the base layer 30 can form a virtually entirely continuous contact surface across the layer (except for at the opening for the collection chamber 12) without fluid channels or other gaps, to provide a strong, secure connection between the device and the body.

Some embodiments of the device disclosed herein advantageously have an uninterrupted skin adhesive layer 40 and/or the base layer 30, at least around the collection chamber 12. In this configuration, the fluids and gases from the wound can be substantially prevented from flowing between the patient's skin and the wound dressing 10, which can lead to leeching of fluids under the skin adhesive and eventual failure of the skin adhesive. For example, when fluids from the wound are allowed to leech under the skin adhesive, the fluids can degrade the effectiveness of the adhesive, which can lead to separation of the wound dressing from the patient's skin. In some embodiments disclosed herein, however, the fluids and gases are diverted above the adhesive and/or base layers into one or more channels disposed between the layers where they are less likely to have deleterious effects on the adhesion of the wound dressing 10 to the patient.

In some embodiments, the skin adhesive layer 40 can be made of a material that is favorable for adhesion to the patient's skin, such as for example a hydrogel polymeric composition. The chemical structure of hydrogel allows it to generally conform to body contours and eliminate most damaging air gaps, while also flexing and stretching with the skin as the body moves without becoming dislodged. Further, it can be reapplied multiple times without losing its adhesive properties. Hydrogel can provide a generally airtight seal over the wound and can absorb wound secretions, does not stick to the wound, can be made transparent to allow for monitoring of the wound without removing the seal, is non-antigenic and non-allergenic, and is easy to store and apply. Some other examples of materials for use as the skin adhesive layer 40 include ethyl carboxyacrylates, polyvinylpyrrolidone and cyanoacrylates. In some embodiments, the top skin layer 40, and one/or more of the other layers, can be at least partially transparent to allow visual inspection of the wound site and/or wound dressing through the layers of the wound dressing 10.

A liner layer 50 can be disposed on the skin adhesive layer 40 to cover and protect the skin adhesive layer 40 from fluids, dirt and other contamination before use. In some embodiments, the size and shape of the liner layer 50 can be generally the same size and shape as the base layer 30 and/or skin adhesive layer 40. In some embodiments, as illustrated, the liner layer 50 can be virtually entirely continuous from side to side, without a cutout for the collection chamber. In some embodiments, as illustrated in FIG. 3, the overall dimensions of the liner layer 50 can be slightly larger than the base layer 30 and/or other layers. In the illustrated embodiment, the length of the liner layer 50 is approximately 168 mm and the width is approximately 127 mm. Many other shapes and sizes can also be used.

In some embodiments, the liner layer 50 can be made of a material that is releasably coupled to the skin adhesive layer 40. For example, the liner layer 50 can be made of a wax coated paper that temporarily adheres to the skin adhesive layer 40, but is easily removable. In some embodiments, the liner layer 50 can be made of other material, such as plastic film, metal foil and the like, that is easily removable from the skin adhesive layer 40.

Figure 4:
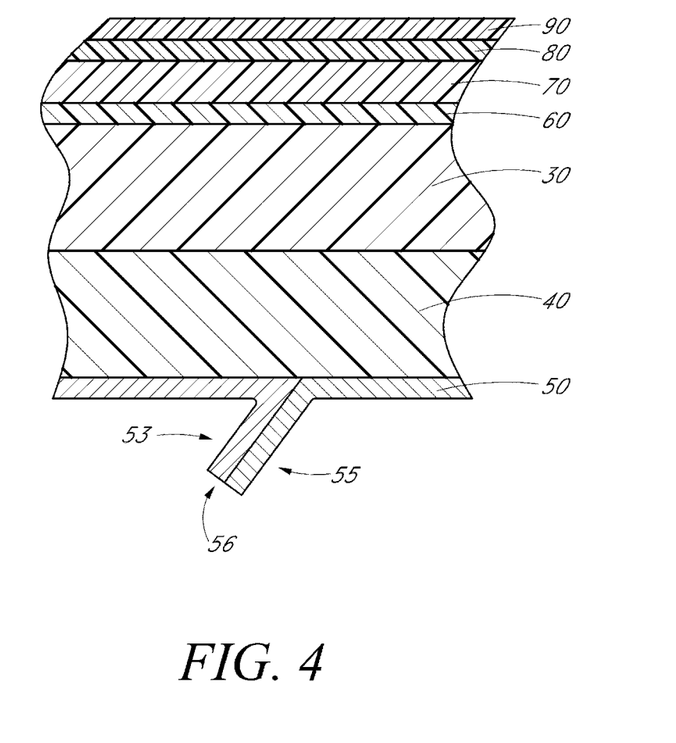
FIG. 4 is a close-up view of detail 4 of FIG. 1.

As illustrated in FIGS. 3 and 4, the liner layer 50 can be made of more than one piece. For example, in the illustrated embodiment, the liner layer 50 is made of a first piece 52 and second piece 54 that meet at a seam 56 that extends along the width of the wound dressing 10. As illustrated in the detail view of FIG. 4, the first piece 52 can have a first tab portion 53 that is not adhered to the skin adhesive layer 40 and the second piece 54 can have a second tab portion 55 that is not adhered to the skin adhesive layer 40. In some embodiments, the tabs 53, 55 can be folded such that they protrude from the surface of the skin adhesive layer 40 and provide an easily graspable portion for removing the liner layer 50. The tabs 53, 55 can be configured for easy grasping, especially while wearing gloves, so that medical personnel on the battlefield can deploy the wound dressing 10 while wearing tactical gear. In some embodiments, the tabs 53, 55 can be marked for quick and easy identification of the tabs during low light or stressful environments. For example, the tabs 53, 55 can be coated with vibrantly colored inks, infrared markers, or luminescent paints.

In some embodiments, the first piece 52 and second piece 54 can include labels or a print layer having indicators that are visible to the user and indicate the sequence for removing the pieces. For example, the first piece 52 can have a "1" or "A" to indicate that it should be removed first. The second piece 54 can have a "2" or "B" signifying that it should be removed second. In some embodiments, the indicator can have a vibrant color, such as red or yellow, for quick and easy identification. In some embodiments, the indicators can reflect visible light or infrared light, or can include luminescent ink for quick and easy identification. The indicators can be sized to be easily visible. In some embodiments, the indicators can be approximately 13 mm in height, and in some embodiments the height can range from at least approximately 3 mm and/or less than or equal to approximately 100 mm.

As illustrated in the embodiment of FIG. 2, the seam 56 can extend along a path that is off-center on the wound dressing 10 such that the seam 56 does not intersect the collection chamber 12. This advantageously helps prevent the inadvertent intrusion of contaminants through the seam 56 into the collection chamber 12. In some embodiments, the liner layer can be a single piece without a seam, but with a tab at a corner or edge of the liner layer for quick and easy removal of the liner layer 50 from the wound dressing 10. In some embodiments, the larger size of the liner layer 50 as compared to the other layers creates border regions along the edges of the liner layer 50 that can be easy grasped to separate the liner layer 50 from the rest of the wound dressing 10, even without tabs.

On top of the base layer 30 can be a top adhesive layer 60 that can have shapes and sizes that are generally similar to those of the base layer 30. An opening or a cutout 62 for the collection chamber can be disposed on the top adhesive layer 60 in a generally similar shape and size as the collection chamber opening or cutout 36 on the base layer 30. In some embodiments, the thickness of the top adhesive layer 60 can be approximately 1 mil. In some embodiments, the thickness can range from approximately 0.5 mil. to approximately 10 mil. In some embodiments, the top adhesive layer 60 can be made of a material that is beneficial for adhering the base layer 30 to the channel layer 70 and top layer 60. Some examples of materials suitable for use as the top adhesive layer 60 include ethyl carboxyacrylates, acrylic cement, and epoxies. In some embodiments, the top adhesive layer 60 can be at least partially transparent to allow visual inspection of the wound site through the wound dressing 10.

As described above for the skin adhesive layer 40, in some embodiments, the top adhesive layer 60 may not cover the entire bottom surface 84 of the top layer 80. For example, in some embodiments, the top adhesive layer can be a bead of adhesive that extends along the outer perimeter of the bottom surface 84 and the perimeter of the cutout 36 on the base layer 30.

With continued reference to FIG. 3, a channel layer 70 can be disposed above the top adhesive layer 60 and can comprise a plurality of pieces in the shapes of the drainage channel 14, vent channel 18, and any other desired channels in the wound dressing 10. The channel layer 70 can be formed from a generally fluid impermeable material, such as plastic, and have top surfaces 72 and bottom surfaces 74. The bottom surfaces of the channel layer 74 can be adhered to the top adhesive layer 60. In the illustrated example, the top surfaces of the channel layer 72 are permitted to move independent of the top layer 80 since they are not adhered to the top layer 80, creating a space between the channel layer 70 and the top layer 80 where air, fluids and exudates can pass from the collection chamber 12 to the exterior. With reference to FIGS. 2 and 3, in some embodiments, the pieces of the channel layer 76, 78 can extend from the collection chamber 12 to the edge of the top layer 86 such that the collection chamber 12 is in fluid communication with the drainage channel outlet 16 through the drainage channel 14, and in fluid communication with the vent channel outlet 20 through the vent channel 18. In some embodiment, valve structures can be disposed in the channel passages formed by the channel layer 70, as discussed below.

In some embodiments, the pieces of the channel layer 76, 78 can be slightly curved in an upwardly convex manner to enhance the opening of the channel passages. For example, the piece for the drainage channel 76 can have sides that are curved upward such that the cross-sectional shape of the drainage channel piece 76 is generally an inverted U-shape. The U-shape can separate the top layer 80 from the concave top surface of the channel layer 72 to help prevent the top layer 80 from collapsing against the channel layer 70, thus forming the passage for the drainage channel 14.

In some embodiments, the channel layer 70 can be made of a semi-rigid or resilient material that can retain its U-shape after transitory compression or distortion, such as for example polyurethane. In some embodiments, the channel layer 70 is compliant so that it can lie flat when packaged, but resilient enough to rebound to its predisposed curved shape when in use. In some embodiments, the channel layer 70 can be made of other materials, such as plastics, metals, or composites. In some embodiments, the channel layer 70 can be at least partially transparent to allow visual inspection of the wound site through the wound dressing 10.

In the embodiment illustrated in FIG. 2, the width of the drainage channel 14 is approximately 38 mm and the width of the vent channel 18 is approximately 19 mm. In some embodiments, the width of the drainage channel can be at least about 20 mm and/or less than or equal to about 60 mm, and the width of the vent channel 18 can be at least about 5 mm and/or less than about 35 mm. Many different sizes and shapes of any piece for the channel layer 70 can be used to suit particular applications and methods of manufacturing. The pieces of the channel layer 70 are not limited to a particular shape or size. In some embodiments, the thickness of the channel layer 70 can be approximately 2 mil. In some embodiments, the thickness can range from approximately 0.5 mil to approximately 10 mil.

The vent channel 18 can help drain the collection chamber 12 or irrigate the wound site by allowing air to exit the collection chamber 12 and prevent buildup of pressure in the patient's chest cavity, which can lead to the condition pneumothorax. As illustrated in FIG. 2, blood and other fluids can flow assisted by gravity through the drainage channel 14 to exit the wound dressing 10, while air in the chest cavity can flow upward through the vent channel 18 to exit the wound dressing 10. Having a drainage channel 14 and a separate vent channel 18 advantageously allows air to escape the chest cavity, even when the drainage channel 14 is congested with draining fluids and exudates.

In some embodiments, more than one drainage channel 14 can be included in the wound dressing 10 to accommodate large drainage flows and allow for multiple drainage paths. In some embodiments, more than one vent channel 16 can be included in the wound dressing 10 for enhanced air venting. In some embodiments, channels for other purposes can be disposed on the wound dressing 10, such as to create a valved working channel for introduction of medication or medical devices.

With reference to FIG. 2, the channel layer 70 can be oriented such that at least one of the longitudinal axes of the channels is askew with the edges of the wound dressing 10. In other words, the longitudinal axis of the channel can be at a non-perpendicular angle α to the edges of the wound dressing 10. For example as illustrated in FIG. 2, the drainage channel 14 is at an angle to the edge of the wound dressing 10. The angle of the drainage channel advantageously allows the fluids from the wound to pool in a small amount at the bottom of the collection chamber 12 before entering the drainage channel 14, which as explained below, can promote proper operation of the drainage channel valve in some embodiments.

Furthermore, when the channels are oriented at acute angles to the edges of the wound dressing, the channel lengths are longer than if the channels were to extend perpendicularly to the edges of the wound dressing 10. The longer lengths can promote better closure and sealing of the channels during valve operation, as described below. In some embodiments, the angle between the longitudinal axis of the channels and the edge of the wound dressing 10 is approximately 60°. In some embodiments, the angle α can be at least approximately 30° and/or less than or equal to approximately 90°.

A top layer 80 can be disposed above the channel layer 70 and above the top adhesive layer 60. In some embodiments, the portions of the top layer 80 that are apposed to the top surface of the channel layer 72 are not adhered to the channel layer 70. The portions of the top layer 80 that contact the top adhesive layer 60 are adhered to the top adhesive layer 60. Thus, a pathway is created between the channel layer 72 and the top layer 80 that directs fluids and air from the collection chamber 12 through the pathway to exit the wound dressing 10. As illustrated in FIG. 3, the top layer 80 can have a virtually entirely continuous surface without an opening or a cutout for the collection chamber. The top layer 80 can serve as a cover to enclose the collection chamber and direct the flow of fluids and exudates through the drainage and vent channels.

In some embodiments, the top layer 80 can be made of a flexible material, such as for example a polyurethane film. In some embodiments, the top layer 80 can be made of other materials, such as plastics, metals, or composites. The top layer 80 can advantageously be made of a clear material to allow the user to visually inspect the collection chamber 12 and channels for any blockages. The clear material can also allow the user to diagnose the patient through visual inspection of the wound site and inspection of the patient's fluids and exudates in the wound dressing 10.

In some embodiments, top layer 80 can be a generally rectangular sheet, similar in shape to the base layer 30. The top layer 80 can be formed from a generally fluid impermeable plastic and have a top surface 82 and bottom surface 84. In some embodiments, the top layer 80 can have generally the same size and shape as the base layer 30. However, many sizes and shapes can be used to suit particular applications and methods of manufacturing, and the top layer 80 is not limited to a particular shape or size. In some embodiments, the thickness of the top layer 80 can be approximately 1 mil. In some embodiments, the thickness can range from approximately 0.5 mil to approximately 10 mil.

A print layer 90 with an indicator 22 can be visible on top of the wound dressing 10. In some embodiments, the print layer 90 can be the topmost layer, but in other embodiments, other layers that are at least partially transparent can be disposed on top of the print layer 90. The print layer 90 can include figures, marks, symbols, labels, etc. that can inform and instruct the user of the proper use of the wound dressing 10. For example, as in the illustrated embodiment, the print layer 90 can include at least one indicator 22 in the shape of an arrow, wherein the wound dressing 10 is to be oriented on the patient such that the arrow points down in the direction of gravity. By pointing the arrows generally in the direction of gravity when attaching the device to a patient, the fluids and exudates from the wound can flow into the collection chamber and gravity can advance the fluids and exudates through the drainage channel 14 and out through the drainage channel outlet 16. In embodiments having a transparent top layer 80 for inspecting the wound site, the indicator 22 can be positioned so as not to obstruct the view into the collection chamber 12 or channels, as illustrated in FIG. 2.

In some embodiments, the print layer 90 can include an indicator that marks the position of the drainage channel outlet 16 and/or the vent channel outlet 20. In some embodiments, the print layer 90 can include instructions and/or warnings for using the wound dressing 10. In some embodiments, the print layer 90 can at least partially include indicators that can be quickly and easily identified in low light or stressful environments. Some examples of such indicators include fluorescent inks, infrared markers, or luminescent paints.

In some embodiments, the top layer 80 and/or print layer 90 can have a textured surface on at least a portion of the top side for providing a non-slip surface to grip the wound dressing 10 when applying it over the skin. In some embodiments, the top layer 80 and/or print layer 90 can have grips or tabs extending from the top side to provide a convenient gripping surface during deployment of the wound dressing 10 to help avoid unwanted contamination of the skin adhesive layer 40 and collection chamber 12.

Some embodiments of the wound dressing 10 can include valves 24 to control the flow of fluid and air. In some embodiments, the valves 24 can be one-way valves that allow air, fluids and exudates to exit the wound, but obstruct fluids or air from entering the wound. The following valve descriptions are examples of some valves that can be used with the wound dressing 10, however, any embodiment of valves can be utilized.

As illustrated in FIGS. 1 and 2, in some embodiments, the valves can be integrally formed by the several layers. For example, a valve can be formed by the top layer 80 and channel layer 70. In an open position, air and fluids are expelled from the wound into the collection chamber 12. The expelled fluids flow from collection chamber 12 into drainage channel 14 and out through the drainage channel outlet 16. The expelled air flows from the collection chamber 12 into the vent channel 18 and out through the vent channel outlet 20. In some embodiments, at least the top layer 80 can flex to separate from the channel layer 70 as air and fluids are directed into the drainage channel 14 and vent channel 18, allowing the exudates to travel between the top layer 80 and channel layer 70.

In a closed position, fluid is not being expelled and the top layer 80 can flex to lie flat against the pieces of the channel layer 76, 78. The negative pressure within the chest cavity can collapse the portion of the top layer 80 against the pieces for the drainage channel 76 and vent channel 78 in a generally fluid- and airtight arrangement. In some embodiments, the negative pressure can draw the portion of the top layer 80 above the collection chamber 12 tightly against the skin of the patient to generally close the fluid and air path. By collapsing under the negative pressure, the top layer 80 generally blocks the inflow of fluid into the chest cavity and maintains the negative pressure of the chest cavity, thus preventing a pneumothorax condition from developing. In embodiments such as this where the top layer 80 is advantageously flexible, pliable material can be used, such as for example polyurethane film or polyethylene film.

Figure 6:
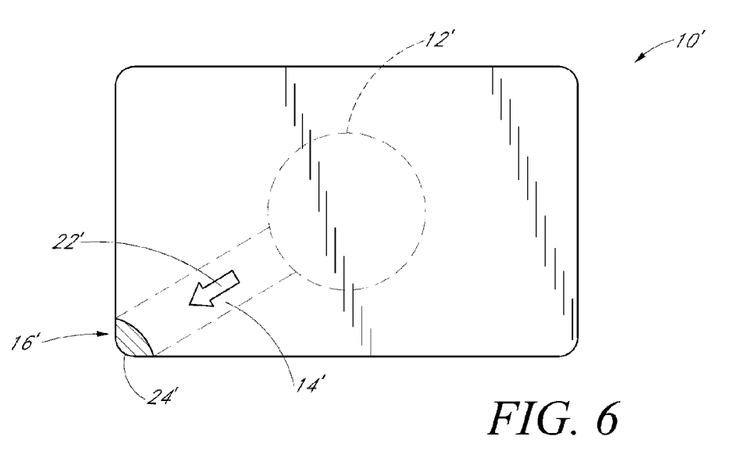
FIG. 6 is a schematic top plan view of a wound dressing according to another embodiment of the present application.

As illustrated in FIG. 6, in some embodiments, the valve can be an additional or a separate component that can be disposed along the flow path of the exudates from the wound. In some embodiments, the valves 24' can be positioned toward the drainage channel outlet 16' and/or the vent channel outlet. The valve can be any type of valve known in the art, such as for example a diaphragm valve, ball valve, swing valve, duckbill valve, etc.

With reference to FIG. 6, the illustrated alternate embodiment is a wound dressing 10' with a collection chamber 12' and a drainage channel 14'. A valve 24' is disposed toward the drainage channel outlet 16' and an indicator 22' in the form of an arrow is placed above the drainage channel 14' to indicate the direction of flow for the wound exudate. In some embodiments, such as the embodiment of FIG. 6, only one channel is present. Therefore, both the air and fluids flow away from the wound from the single channel.

Figure 7:
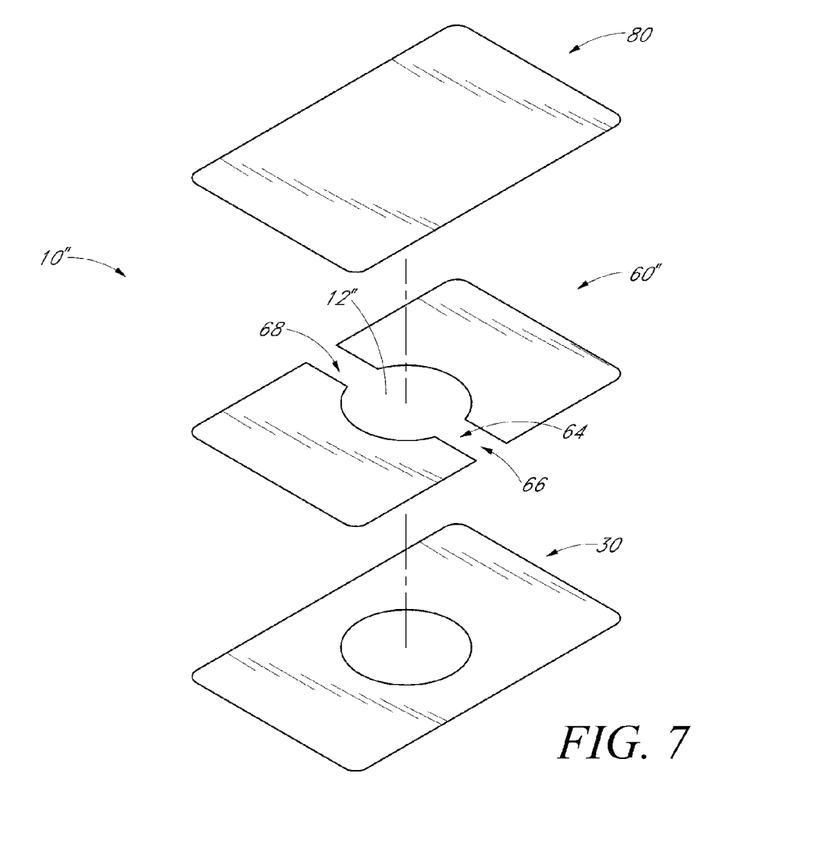
FIG. 7 is a schematic exploded top perspective view of a wound dressing according to another embodiment of the present application.

FIG. 7 illustrates a portion of an alternate embodiment of the wound dressing. As illustrated in FIG. 7, in some embodiments, a drainage channel 64 can be formed integrally by the top adhesive layer 60" by the absence of adhesive from a selected area of the top adhesive layer 60" extending radially outward from the collection chamber 12" to a drainage channel outlet 66 at a peripheral edge of the top adhesive layer 60" to drain fluids and exudates from the collection chamber 12". The air and fluids are enclosed on the bottom side by the base layer 30 and on the top side by the top layer 80, as illustrated in FIG. 7. In some embodiments, a plurality of drainage channels can be formed by the top adhesive layer 60" to handle large amounts of evacuation. In some embodiments, the adhesive layer can include a vent channel 68 formed by the absence of adhesive from a selected area of the top adhesive layer 60" extending radially outward from the collection chamber 12", similar to the drainage channel 64. In some embodiments, the width of the pathway through the adhesive which forms the drainage channel 64 can be approximately 38 mm and the width of the adhesive pathway which forms the vent channel 68 can be approximately 19 mm.

In some embodiments, the wound dressing 10" can have a collection chamber 12", but no channel layer, such that the collection chamber 12" is enclosed and sealed off from the surroundings. Thus, the wound dressing 10" in these embodiments can seal the wound and prevent air, fluids or contaminants from entering the wound. This embodiment of the wound dressing 10" can be used to treat a piercing entry wound, where there is typically limited bleeding, but is advantageously sealed to treat pneumothorax.

Figure 8:
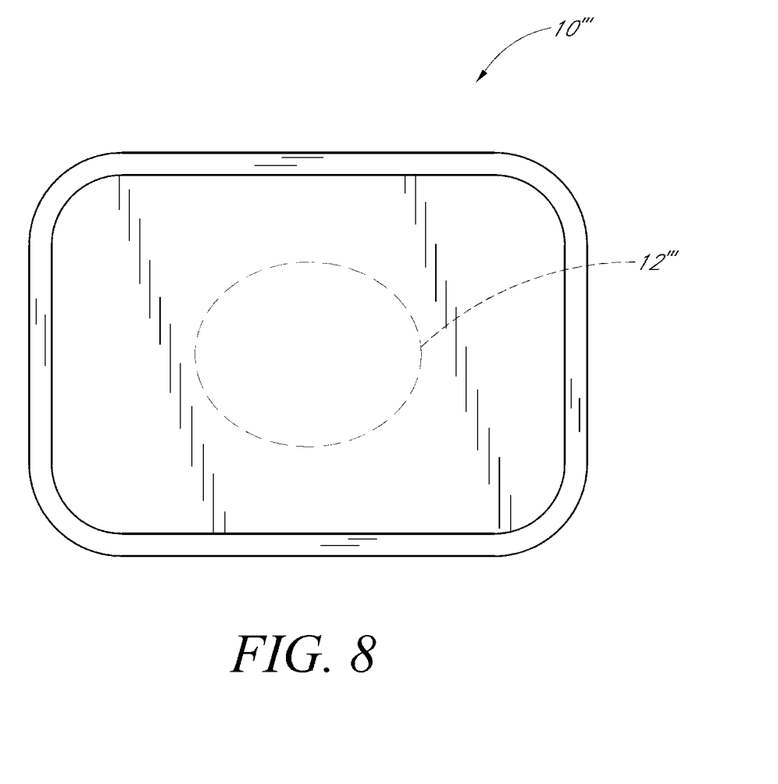
FIG. 8 is a schematic top plan view of a wound dressing according to another embodiment of the present application.

In circumstances where there is an exit wound (rather than an entry wound), a pneumothorax condition can be treated by covering the exit wound using an embodiment of the wound dressing having drainage channels and vent channels, as described above. Thus, a patient suffering from pneumothorax can be treated with a combination of different embodiments of the present device. For example, the entry wound can be sealed with the embodiment of the wound dressing 10" illustrated in FIG. 8, and the exit wound can be treated with an embodiment of the wound dressing 10 illustrated in FIG. 1-3.

In some embodiments, the excess pressure which has accumulated in the pleural space of the chest can be relieved by other means, such as by needle decompression. This can involve inserting a large-bore 14-16 gauge needle into the patient's chest (e.g., through a valve in the device 10 or directly into the chest). In some embodiments, a catheter can also be inserted into the chest in a similar manner. Once the needle is in the pleural space, the air escapes through the catheter which remains in place while the needle is removed.

In some embodiments, the wound dressing can include a monitoring device that indicates to the medical personnel when the patient is venting air and/or when the patient has vented air from the chest. The monitoring device can also have an indicator that informs the medical personnel of the number of time that the patient has vented air. In some embodiments, the monitoring device can be electronic. Various embodiments and descriptions of monitoring devices are disclosed in U.S. Patent Application No. 61/231,888, filed Aug. 6, 2009, the entirety of which is incorporated by reference herein.

Some examples of methods of using the wound dressings disclosed herein will now be described. When medical personnel or other users of the wound dressing, comes upon a patient with a penetrating wound, the medical personnel can identify the type and severity of the wound and select the wound dressing most suitable for the situation. For exit wounds which may have larger trauma areas, the medic can select an embodiment of the wound dressing having a drainage channel and vent channel. For patients suffering from pneumothorax, a wound dressing having a one-way valve can be employed. A plurality of devices 10 with different sizes of layer surface area and collection chamber cross-sectional widths can be used depending on the size of the wound to be treated.

In some embodiments, the medical personnel can prepare for adhesion of the wound dressing by cleaning the area surrounding the wound site of dirt, blood and fluids. The wound dressing can be removed from a sterilized protective wrapper or packaging and prepared for application. The liner layer can be pulled and removed from the wound dressing. The wound dressing can be placed over the wound site with the collection chamber generally centered over the center of the wound. In embodiments where the liner layer has two pieces, such as in the illustrated embodiments of FIGS. 1-3, the smaller liner layer piece can be removed first. In some embodiments, the smaller liner layer can have an indicator, such as a "1" or "A", as described above, that indicates that the small liner layer is to be removed first. While grasping the parts of the wound dressing still covered by the larger liner layer piece, the portion of the wound dressing with the exposed skin adhesive layer can be attached to the patient. Then, the larger liner layer piece, which in some embodiments can have the next sequential indicator, such as a "2" or "B", can be peeled off while simultaneously applying the exposed skin adhesive layer to the patient's skin. This technique can minimize contamination of the wound dressing during application.

Figure 5:
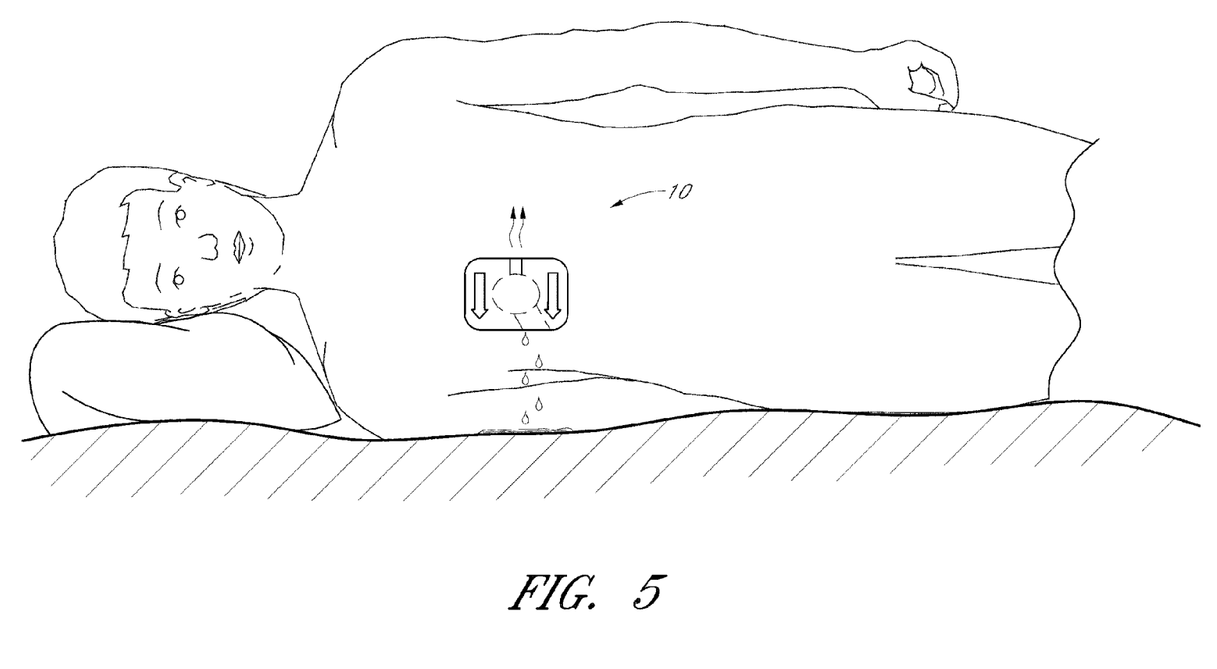
FIG. 5 is a schematic top plan view of the wound dressing of FIG. 1 applied to a wound on a patient's body.

With reference to FIG. 5, the wound dressing 10 can be oriented so that the indicators, which are shown as arrows in the illustrated embodiment, are pointed generally downward. This can orient the drainage channel to flow generally downward with gravity and the vent channel upward. The air and fluids expelled from the wound can collect in the collection chamber. The fluids can flow, assisted by gravity, from the collection chamber to the drainage channel and out through the drainage channel outlet, where the fluids can be expelled from the wound dressing. In some embodiments, the fluids can pool slightly at the bottom of the collection chamber before entering the drainage channel. The fluid pooling can advantageously meter the flow of fluids through the drainage channel to avert circumstances where the drainage channel valve can become stuck in the open position when the flow rate through the drainage channel is too high. The air can flow independently from the fluids, from the collection chamber into the vent channel, where it is expelled from the wound dressing through the vent channel outlet.

In embodiments of the wound dressing having valves, the fluids and exudates can exit the wound dressing by passing through the valves in one direction, or the valves can be configured to permit passage of other medical implements for treatment of the wound. However, gases and fluids from the environment are not able to enter into the wound in the other direction through the valves, thus enabling the wound dressing to treat conditions such as pneumothorax.

In some embodiments, the wound dressing can be repositioned on the patient's skin if the initial positioning is incorrect or insufficient to treat the wound. The skin adhesive layer can be configured to be removed and reapplied without substantially losing its adhesive abilities. In some circumstances, the wound dressing may need to be removed to clean or treat the wound before the wound dressing is reapplied.

Although certain embodiments, features, and examples have been described herein, it will be understood by those skilled in the art that many aspects of the methods and devices illustrated and described in the present disclosure may be differently combined and/or modified to form still further embodiments. For example, it is contemplated that any component of the wound dressing illustrated and described above can be used alone or with other components. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

The following is claimed:

1. A dressing for treating a wound, the dressing comprising:
   a base layer comprising a first aperture extending through the base layer;
   a first adhesive layer coupled to a first side of the base layer and comprising a second aperture extending through the first adhesive layer;
   a second adhesive layer coupled to a second side of the base layer and comprising a third aperture extending through the second adhesive layer;
   a channel layer comprising at least one member coupled to portions of the second adhesive layer; and
   a top layer coupled to at least portions of the second adhesive layer and apposed to the channel layer, wherein a channel is formed between the channel layer and the top layer, the channel extending from the third aperture to an edge of the second adhesive layer;
   wherein the first aperture, second aperture, and third aperture are generally aligned to form a collection chamber that is in fluid communication with the channel;
   wherein the top layer is configured to have a closed position relative to the channel layer, wherein the top layer is configured to collapse against the channel layer to form a generally fluid tight arrangement between the top layer and the channel layer.

2. The dressing of claim 1, further comprising a liner layer coupled to the first adhesive layer.

3. The dressing of claim 2, wherein the liner layer comprises a tab to facilitate removal of the liner layer.

4. The dressing of claim 3, wherein the liner layer comprises at least two portions that join along a seam.

5. The dressing of claim 1, further comprising a print layer coupled to the top layer.

6. The dressing of claim 5, wherein the print layer comprises a mark indicating a direction of flow through the dressing.

7. The dressing of claim 1, further comprising at least one valve that restricts air and fluids from entering the wound.

8. The dressing of claim 1, wherein the channel layer comprises a drainage channel member and a vent channel member.

9. The dressing of claim 1, wherein at least one of the base layer, channel layer or top layer is made of polyurethane.

10. The dressing of claim 1, wherein the channel layer comprises at least one piece that is concave and curved upward.

11. The dressing of claim 1, wherein the first adhesive layer is configured to adhere to a patient's skin.

12. A dressing for treating wounds, the dressing comprising:
   a first layer;
   a second layer over the first layer;
   a third layer over the second layer;
   a fourth layer over the third layer; and
   a collection chamber formed by an aperture extending through the first layer, second layer and third layer;
   a channel that extends from the collection chamber to an edge of the dressing, wherein the channel is configured to have a closed position in which the channel is configured to collapse to form a generally fluid tight arrangement.

13. The dressing of claim 12, wherein the channel is formed by:

a fifth layer disposed in at least portions between the third layer and fourth layer;

wherein the channel is in fluid communication with the collection chamber in an open position.

14. The dressing of claim 12, wherein the channel is formed by an exclusion of material from the third layer, wherein the channel is in fluid communication with the collection chamber.

15. The dressing of claim 12, wherein the first layer is configured to adhere to a patient's skin.

16. The dressing of claim 12, wherein the third layer is an adhesive coupled to the second layer and fourth layer.

17. A method of treating a wound comprising the steps of:

opening a package containing a wound dressing, the wound dressing comprising at least four layers and having a collection chamber and a drainage channel, wherein the drainage channel extends from the collection chamber to an edge of the dressing, and the drainage channel is configured to have a closed position in which the drainage channel is configured to collapse to form a generally fluid tight arrangement;

preparing the wound dressing by exposing a first adhesive layer that is configured to attach to skin;

orienting the wound dressing using an indicator visible on the wound dressing so that the drainage channel is directed downward in the direction of gravity; and placing the wound dressing on a patient so that the collection chamber is generally centered over the wound.

18. The method of claim 17, wherein the wound dressing further comprises a valve that allows air and fluids to exit the wound, but restricts air and fluids from entering the wound.

* * * * *